US00PP10217P

United States Patent [19]

Wain

[11] Patent Number: Plant 10,217

[45] Date of Patent: Jan. 27, 1998

[54] CHRYSANTHEMUM PLANT NAMED 'RED START'

[75] Inventor: Peter Wain, Portsmouth, United Kingdom

[73] Assignee: Cleangro Ltd., Chichester, United Kingdom

[21] Appl. No.: 733,726

[22] Filed: Oct. 18, 1996

[51] Int. Cl.[6] ..... A01H 5/00

[52] U.S. Cl. ..... Plt./82

[58] Field of Search ..... Plt./76, 82

[56] References Cited

U.S. PATENT DOCUMENTS

P.P. 9,585 6/1996 Glicenstein ..... Plt./82

*Primary Examiner*—Howard J. Locker

*Attorney, Agent, or Firm*—C. A. Whealy

[57] ABSTRACT

A distinct cultivar of Chrysanthemum plant named 'Red Start', characterized by its vigorous, upright and uniform growth habit; freely branching plant habit; decorative-type inflorescences; bronze-red colored ray florets; numerous inflorescences per plant; and good garden performance.

2 Drawing Sheets

1

The present invention relates to a new and distinct cultivar of Chrysanthemum plant, botanically known as *Dendranthema grandiflora* and referred to by the cultivar name Red Start.

The new cultivar is a product of a planned breeding program conducted by the inventor in Chichester, West Sussex, United Kingdom. The objective of the breeding program was to create new Chrysanthemum cultivars having desirable inflorescence colors and good garden performance.

The new cultivar originated from a cross made by the inventor of the cultivar Bravo (U.S. Plant Pat. No. 6,888) as the female, or seed, parent with the proprietary selection 7/GM/94 as the male, or pollen, parent.

The new Chrysanthemum was discovered and selected by the inventor as a flowering plant within the progeny of the stated cross in a controlled environment in Chichester, West Sussex, United Kingdom.

Asexual reproduction of the new cultivar by terminal cuttings taken at Chichester, West Sussex, United Kingdom, has shown that the unique features of this new Chrysanthemum are stable and reproduced true to type in successive generations.

The following traits have been repeatedly observed and are determined to be the unique characteristics of 'Red Start'. These characteristics in combination distinguish 'Red Start' as a new and distinct cultivar:

1. Vigorous, upright and uniform growth habit.
2. Freely branching plant habit.
3. Decorative-type inflorescences.
4. Bronze-red colored ray florets.
5. Numerous inflorescences per plant.
6. Good garden performance.

The cultivar Red Start has not been observed under all possible environmental conditions. The phenotype may vary somewhat with variations in environment such as temperature, daylength and light intensity, without, however, any variance in genotype.

In side-by-side comparisons in Chichester, West Sussex, United Kingdom, under commercial practice, plants of the new Chrysanthemum have more ray florets, a more uniform plant habit, are more compact, and flower later than plants of the male parent, the proprietary selection 7/GM/94.

Plants of the new Chrysanthemum can be compared to the female parent, the cultivar Bravo. However, in side-by-side comparisons conducted in Oxnard, Calif., under commercial practice, plants of the new Chrysanthemum differed from plants of the cultivar Bravo in the following characteristics:

2

1. Plants of the new Chrysanthemum are shorter and more uniform than plants of the cultivar Bravo.
2. Plants of the new Chrysanthemum are more freely branching than plants of the cultivar Bravo.
3. Plants of the new Chrysanthemum have shorter leaves than plants of the cultivar Bravo.
4. Plants of the new Chrysanthemum flower about 5 to 7 days later than plants of the cultivar Bravo.
5. Inflorescences of plants of the new Chrysanthemum have better substance than inflorescences of plants of the cultivar Bravo.
6. Ray florets of plants of the new Chrysanthemum are spoon-shaped whereas ray florets of plants of the cultivar Bravo are obovate in shape.
7. Inflorescences of plants of the new Chrysanthemum have more ray florets than inflorescences of plants of the cultivar Bravo.
8. Plants of the new Chrysanthemum have shorter peduncles than plants of the cultivar Bravo.

A detailed comparison of plants of the new Chrysanthemum and the cultivar Bravo appears in Chart A at the end of the specification.

The accompanying colored photographs illustrate the overall appearance of the new cultivar, showing the colors as true as it is reasonably possible to obtain in colored reproductions of this type.

The first photograph comprises a top perspective view of a typical flowering 16.5-cm container of 'Red Start' with one cutting in the container.

The second photograph comprises a close-up view of five leaves at different stages of development and a fully opened inflorescence. Foliage and floret colors in the photographs may appear different from the actual colors due to light reflectance.

In the following description, color references are made to The Royal Horticultural Society Colour Chart except where general terms of ordinary dictionary significance are used. The following observations and measurements describe plants grown in Oxnard, Calif., under commercial practice in a glass-covered greenhouse with average night temperatures of 18C, average day temperatures of 30C, and light levels of 2,000 (cloudy conditions) to 9,000 (sunny conditions) footcandles.

After sticking unrooted cuttings of the new cultivar, plants received 4 weeks of long day/short nights followed by short day/long nights until flowering. Measurements and numerical values represent ranges or averages for six typical flowering plants.

Botanical classification: *Dendranthema grandiflora* cultivar Red Start.

Commercial classification: Garden chrysanthemum.

Parentage:

*Female, or seed, parent.*—*Dendranthema grandiflora* cultivar Bravo (U.S. Plant Pat. No. 6,888).

*Male, or pollen, parent.*—*Dendranthema grandiflora* proprietary selection 7/GM/94.

Propagation:

*Type.*—Terminal tip cuttings.

*Time to roofing.*—10 to 12 days with soil temperatures of 20C.

*Rooting habit.*—Fine, fibrous and well-branched.

Plant description:

*Appearance.*—Perennial herbaceous garden plant. Vigorous and rapid growth rate. Stems upright, uniform habit and freely branching.

*Plant height.*—About 23 cm.

*Lateral branch length.*—About 19 cm.

*Quantity of lateral branches after removal of apical meristem.*—4 to 5.

*Stem color.*—146D.

*Foliage description.*—Number of leaves per plant: About 60. Number of leaves per lateral branch: About 16. Leaf arrangement: Alternate. Leaf size, fully expanded: Length: About 4.8 cm. Width: About 4.75 cm. Leaf apex: Rounded, slightly apiculate. Leaf base: Attenuate. Leaf margin: Palmately lobed. Leaf texture: Abaxial and adaxial surfaces slightly pubescent, smooth and dull. Veins prominent on abaxial surface. Petiole length: About 2.4 cm. Color: Young foliage adaxial surface: 146A. Young foliage abaxial surface: 146B. Fully expanded foliage adaxial surface: 146A. Fully expanded foliage abaxial surface: 146B. Venation abaxial surface: 146B. Venation adaxial surface: 146B. Petiole: 147C.

Flowering description:

*Appearance.*—Decorative inflorescence form. Inflorescences borne on terminals above foliage, arising from leaf axils. Disc and ray florets arranged acropetally on a flat capitulum.

*Flowering response.*—Under natural conditions, plants flower in the autumn. At other times of the year, inflorescence initiation and development can be induced under short day/long night conditions (at least 13.5 hours of darkness). Plants exposed to about 4 weeks of long day/short night conditions after sticking followed by photoinductive short day/long night conditions, flower about 54 days later.

*Quantity of inflorescence.*—About 6 to 8 inflorescences per flowering stem.

*Inflorescence size.*—Diameter: About 4.2 cm. Depth (height): About 1.7 cm. Diameter of disc: About 2 min.

*Opening inflorescences.*—Bud shape: Spherical. Bud size: Length: About 8 mm. Width: About 8 mm. Bud color: 184A.

*Ray florets.*—Shape: Spoon-shaped. Size: Length: About 2 cm. Width: About 6 mm. Apex: Irregularly dentate. Base: Acute. Margin: Entire. Texture: Velvety, slightly ridged and glabrous. Aspect: Flat. Number of ray florets per inflorescence: About 116. Color: When opening, adaxial surface: 185A. When opening, abaxial surface: 181B. Mature, adaxial surface: 180A. Mature, abaxial surface: 179C. Fading to: 180B.

*Disc florets.*—Shape: Tubular. Size: Length: About 4 min. Width: About 1 mm. Number of disc florets per inflorescence: About 5. Color: Immature: 154D. Mature: 154C.

*Peduncle.*—Aspect: Strong and angled about 25° to 30° to the stem. Length: First peduncle: About 3.5 cm. Fourth peduncle: About 4.8 cm. Texture: Pubescent. Color: 146B.

*Reproductive organs.*—Androecium: Present on disc florets only. Anther color: 12A. Pollen: Moderate, 12A in color. Gynoecium: Present on both ray and disc florets. Style color: 154B.

Disease resistance: No known Chrysanthemum diseases observed to date on plants grown under commercial greenhouse conditions.

Seed production: Seed production has not been observed.

CHART A

| CHARACTERISTIC | 'RED START' | 'BRAVO' |
|---|---|---|
| PLANT HEIGHT | About 23 cm | About 26 cm |
| LATERAL STEM LENGTH | About 19 cm | About 21 cm |
| QUANTITY OF LATERAL BRANCHES AFTER PINCHING | 4 to 5 | About 3 |
| LEAF LENGTH | About 4.8 cm | About 5.8 cm |
| LEAF WIDTH | About 4.75 cm | About 4.3 cm |
| YOUNG FOLIAGE, ADAXIAL | 146A | 137A |
| YOUNG FOLIAGE, ABAXIAL | 146B | 137C |
| MATURE FOLIAGE, ADAXIAL | 146A | 137A |
| MATURE FOLIAGE, ABAXIAL | 146B | 137C |
| RESPONSE TIME | About 54 days | About 49 days |
| BUD COLOR | 184A | 181C |
| RAY FLORET SHAPE | Spoon | Obovate |
| RAY FLORET LENGTH | About 2 cm | About 1.85 cm |
| RAY FLORET WIDTH | About 6 mm | About 4.5 mm |
| RAY FLORET COLOR, WHEN OPENING, ADAXIAL | 185A | 185A |
| RAY FLORET COLOR, WHEN OPENING, ABAXIAL | 181B | 185B |
| RAY FLORET COLOR, MATURE, ADAXIAL | 180A | 46A |
| RAY FLORET COLOR, MATURE, ABAXIAL | 179C | 179D |
| RAY FLORET COLOR FADING TO | 180B | 180A |
| NUMBER OF RAY FLORETS PER INFLORESCENCE | About 116 | About 62 |
| PEDUNCLE LENGTH, FIRST | About 3.5 cm | About 4 cm |
| PEDUNCLE LENGTH, FOURTH | About 4.8 cm | About 6 cm |

It is claimed:

1. A new and distinct cultivar of Chrysanthemum plant named 'Red Start', as illustrated and described.

* * * * *

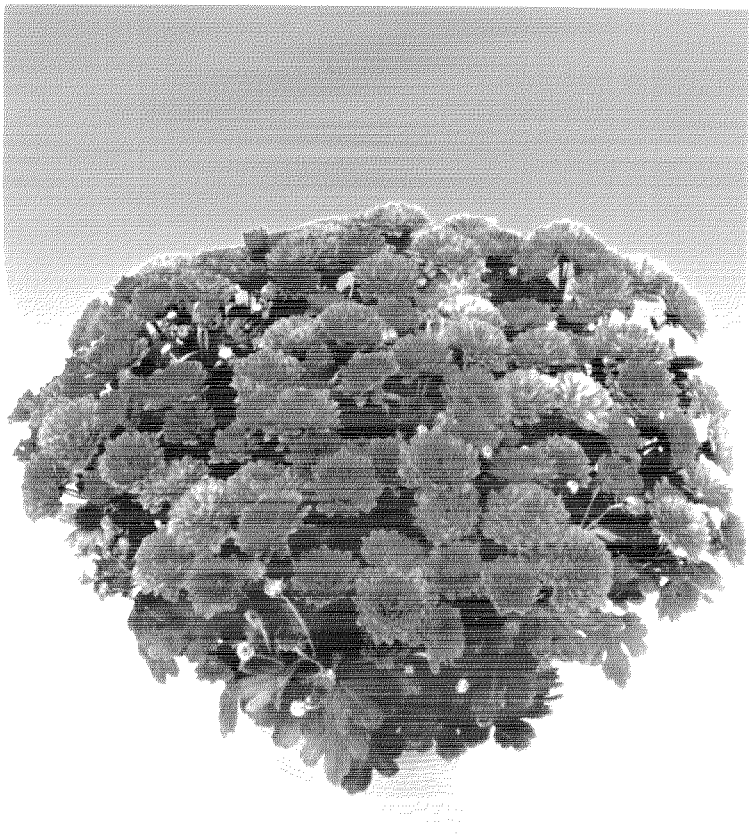

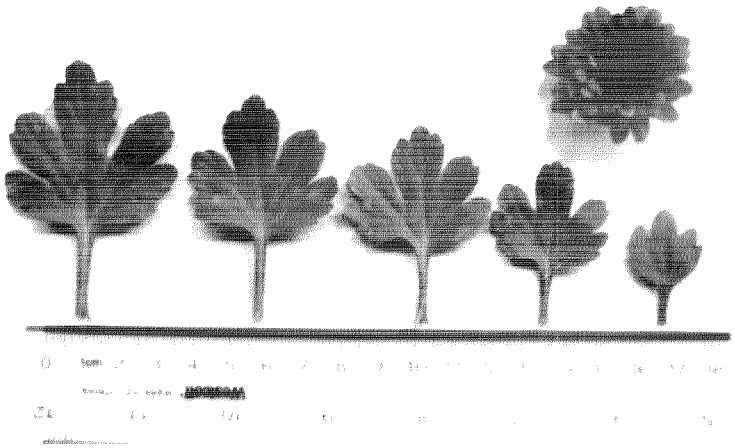

UNITED STATES PATENT AND TRADEMARK OFFICE

CERTIFICATE OF CORRECTION

PATENT NO. : Plant 10,217
DATED : January 27, 1998
INVENTOR(S) : Peter Wain

It is certified that error appears in the above-indentified patent and that said Letters Patent is hereby corrected as shown below:

Column 3, line 11, change "roofing" to -- rooting --.
Column 3, line 55, change "min." to -- mm. --.
Column 4, line 11, change "min." to -- mm --.

Signed and Sealed this
Fifth Day of January, 1999

*Attest:*

*Attesting Officer*

*Acting Commissioner of Patents and Trademarks*